United States Patent

Townend et al.

[11] Patent Number: 5,985,815
[45] Date of Patent: Nov. 16, 1999

[54] BLEACH ACTIVATORS

[75] Inventors: John Townend; Jan Darrel Crowther, both of Clwyd, United Kingdom

[73] Assignee: Warwick International Group Limited, United Kingdom

[21] Appl. No.: 08/648,104

[22] PCT Filed: Nov. 25, 1994

[86] PCT No.: PCT/GB94/02584

§ 371 Date: Apr. 3, 1997

§ 102(e) Date: Apr. 3, 1997

[87] PCT Pub. No.: WO95/14760

PCT Pub. Date: Jun. 1, 1995

[30] Foreign Application Priority Data

| Nov. 25, 1993 | [GB] | United Kingdom | 9324261 |
| Dec. 16, 1993 | [GB] | United Kingdom | 9325777 |
| Dec. 23, 1993 | [GB] | United Kingdom | 9326382 |
| Dec. 23, 1993 | [GB] | United Kingdom | 9326383 |
| Dec. 23, 1993 | [GB] | United Kingdom | 9326384 |
| Dec. 23, 1993 | [GB] | United Kingdom | 9326385 |
| Aug. 5, 1994 | [GB] | United Kingdom | 9415871 |

[51] Int. Cl.$^6$ .............. C11D 3/39; C09K 3/00; C07D 223/10; C07D 207/27; C07D 211/76; C07D 403/14; C07C 409/40

[52] U.S. Cl. .............. 510/313; 252/186.39; 562/2; 540/200; 540/485; 546/243; 546/245; 546/278.4; 546/278.7; 546/290; 546/298; 548/520; 548/521; 548/543

[58] Field of Search .............. 252/186.39; 540/200, 540/485; 546/243, 245, 278.4, 278.7, 290, 298; 562/2; 548/520, 521, 543; 510/313

[56] References Cited

U.S. PATENT DOCUMENTS

| 2,813,896 | 11/1957 | Krimm | 562/2 |
| 3,655,738 | 4/1972 | Nielsen | 562/6 |
| 3,816,324 | 6/1974 | Fine et al. | 424/616 |
| 3,982,891 | 9/1976 | Murray | 8/111 |
| 4,134,850 | 1/1979 | McCrudden et al. | 252/186.26 |
| 4,259,201 | 3/1981 | Cockrell, Jr. et al. | 510/310 |
| 4,634,551 | 1/1987 | Burns et al. | 510/313 |
| 4,751,015 | 6/1988 | Humphreys et al. | 510/376 |
| 5,149,864 | 9/1992 | Gethoffer et al. | 562/2 |
| 5,268,003 | 12/1993 | Coope et al. | 8/111 |
| 5,292,451 | 3/1994 | Gethoffer et al. | 252/186.42 |
| 5,503,639 | 4/1996 | Willey et al. | 8/111 |
| 5,560,862 | 10/1996 | Gosselink et al. | 252/186.39 |

FOREIGN PATENT DOCUMENTS

| 0027693 | 4/1981 | European Pat. Off. . |
| 0043173 | 1/1982 | European Pat. Off. . |
| 0083560 | 7/1983 | European Pat. Off. . |
| 0136280 | 4/1985 | European Pat. Off. . |
| 0168204 | 1/1986 | European Pat. Off. . |
| 0168587 | 1/1986 | European Pat. Off. . |
| 0170386 | 2/1986 | European Pat. Off. . |
| 0186650 | 7/1986 | European Pat. Off. . |
| 0325288 | 7/1989 | European Pat. Off. . |
| 0325289 | 7/1989 | European Pat. Off. . |
| 0331300 | 9/1989 | European Pat. Off. . |
| 0332050 | 9/1989 | European Pat. Off. . |
| 0349940 | 1/1990 | European Pat. Off. . |
| 0366041 | 5/1990 | European Pat. Off. . |
| 0426217 | 5/1991 | European Pat. Off. . |
| 0564250 | 10/1993 | European Pat. Off. . |
| 0332294 | 9/1994 | European Pat. Off. . |
| 3906768 | 9/1990 | Germany . |
| 0855735 | 12/1960 | United Kingdom . |
| 93/06203 | 9/1991 | WIPO . |
| 92/11238 | 7/1992 | WIPO . |
| 94/18298 | 2/1994 | WIPO . |

*Primary Examiner*—Joseph D. Anthony
*Attorney, Agent, or Firm*—Morgan & Finnegan, L.L.P.

[57] ABSTRACT

New compounds useful as bleach activators as well as new percarboxylic acids, which may be formed as intermediates upon reaction of such activators with peroxygen bleach source in aqueous solution, include nitrogen-containing heterocyclic groups. Preferred activators are symmetrical derivatives of dibasic carboxylic acids, having N,N'diacyl N-heterocyclic groups usually lactams. They are produced by reaction of 2 moles of the lactam with one mole of dibasic acid chloride or anhydride.

15 Claims, No Drawings

BLEACH ACTIVATORS

This application is a 371 of PCT/GB94/02584, filed Nov. 25, 1994.

The present invention relates to new compounds used as bleach activators, compositions containing peroxygen bleach source and said activator compounds, processes in which the activator compound and peroxygen bleach source are reacted to produce a stronger oxidising species and some novel products of such a reaction, its use as an oxidising agent, for instance a bleach or biocide.

It is very well known in the laundry detergent field to use a combination of peroxygen bleach precursor (or peroxygen source) and bleach activator in the same or separate compositions. The bleach activators are usually acyl-donors. During storage of a composition including peroxygen bleach source and bleach activator, the two components are prevented from contacting one another under conditions such that the perhydrolysis reaction would take place.

Percarboxylic acids of various types have been used as bleaching species. Mono- and di- peroxydicarboxylic acids are described in, for instance, U.S. Pat. No. 3,655,738 (diperphthalic acid is described). In U.S. Pat. No. 4,134,850, mono- and poly- peroxy acid derivatives of cyclohexyl di- and multi- carboxylic acid compounds are described. In EP-A-0,027,693 magnesium salts of monoperoxy dicarboxylic aromatic or cycloaliphatic acids are produced and used in detergent compositions. In U.S. Pat. No. 2,813,896 and U.S. Pat. No. 4,259,201 $\alpha,\omega$-long chain aliphatic diperoxoic acids are described as bleaching agents. The third compounds are diperoxy dodecanedioic acid, diperoxy azelaic acid and diperoxy adipic acid. Substituted butane diperoxoic acids are also known from EP-A-0,083,560 and EP-A-0,136,280, EP-A-0,186,650, EP-A-0,179,233 and EP-A-0168587.

The use of percarboxylic acids in which the molecule includes an amide linkage is described in EP-A-0,170,386. The amide linkage in the carboxylic acid molecule may have either the nitrogen or the carbonyl group closer to the percarboxylic acid moiety. This citation describes further the use of magnesium salts of the peroxy acids in detergent compositions or the use of activators which produce the peroxy acid in situ by reaction with peroxygen bleach source. The activators include an acyl moiety (ultimately forming the percarboxylic acid) and a leaving group. Examples of activators include various N-acyl compounds, including compounds in which the nitrogen atom is part of a heterocyclic ring, examples being imidazole rings and optionally substituted hydantoin rings. Examples of acyl moieties of the percarboxylic acid formed are all aryl derivatives and no examples of any other cyclic moieties are disclosed.

Other examples of nitrogen-containing percarboxylic acids used as oxidising/bleaching agents are succinimides and phthalimides of $\omega$-amino alkaneperoxoic acids are described in EP-A-0,325,289, EP-A-3,252,88, EP-A-0,366, 041, EP-A-0,349,940 and DE-A-3,906,768. The peracids themselves are said to be sufficiently stable to incorporate directly into detergent compositions. However the peracids, as well as their salts are still of limited stability in a detergent composition.

N-acyl lactams have been used as activators. In GB-A-0,855,735 various N-acyl organo amides, in which the nitrogen atom is part of a heterocyclic ring are described, including N-acetyl saccharin, N-acetyl phthalamide and N-acetyl caprolactam. U.S. Pat. No. 3,982,891 describes imides including a N-bonded substituent of the formula COOR such as N-alkoxycarbonyl-saccharides, phthalimides, succinimides and hydantoins.

Other amide group containing peroxy acid bleaching species are described in U.S. Pat. No. 5,268,003, where the compounds include at least two peroxoic carboxylic acid groups joined by a dibasic group which includes at least two amide groups. Where the nitrogen atoms of both amide groups are located towards the center of the molecule, the nitrogen atoms may each have substituents which are joined so that a heterocyclic group containing both nitrogen atoms is present.

Other nitrogen containing bleach activators are isatoic anhydride derivatives such as are described in EP-A-0,332, 050 and EP-A-0,331,300. In EP-A-0,332,294, 2-substituted oxazine-4-one compounds, usually (4H)3,1-benzoxazine-4-one derivatives, are described as bleach activators.

A new compound forming the first aspect of the present invention, for use as a bleach activator, has the formula I

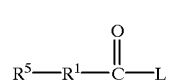

in which L is a leaving group the conjugate acid of which has $pK_a$ 4–13 (preferably 6–11, more preferably 8–11) and which includes a nitrogen containing heterocycle, $R^1$ is an alkylene group having 1–50 carbon atoms, optionally interrupted by one or more ether, ester, anhydride, thioether, 2° or 3° amine, amide or imide linkages, and $R^5$ is an organic group comprising a nitrogen-containing heterocycle.

In this aspect of this invention the group L is preferably joined to the carbonyl carbon atom via the said nitrogen atom. The leaving group may be any of those nitrogen-containing heterocyclic leaving groups described in the prior art as such. The heterocycle generally comprises a carbonyl group in the ring adjacent the nitrogen atom joined to the carbonyl group shown in the formula I, although N-imidazole may constitute the leaving group L. Preferred leaving groups are for instance uracils, hydantoins, glycol urils, 2,5-diketopiperazine and, preferably, N-lactam groups.

The heterocyclic ring may contain 4–10 atoms, preferably 5 atoms, more preferably 6–8 atoms. The heterocyclic ring may contain other heteratoms, such as sulphur and/or oxygen atoms and may be saturated or fully or partially unsaturated. The heterocyclic ring may furthermore be substituted, for instance at nitrogen or carbon atoms and may include substituted cyclic groups, for instance fused aromatic or saturated ring systems. For instance the leaving group may include an isatoic anhydride derivative, for instance joined via the nitrogen atom of the isatoic anhydride moiety. Another example of a nitrogen containing leaving group is a 2-substituted oxazine-4-one derivative, preferably a (4H) 1,3-benzoxazine-4-one derivative, for instance joined to the carbonyl group of the formula I via the two-position.

Specific examples of suitable groups L are furthermore exemplified by the following structures:

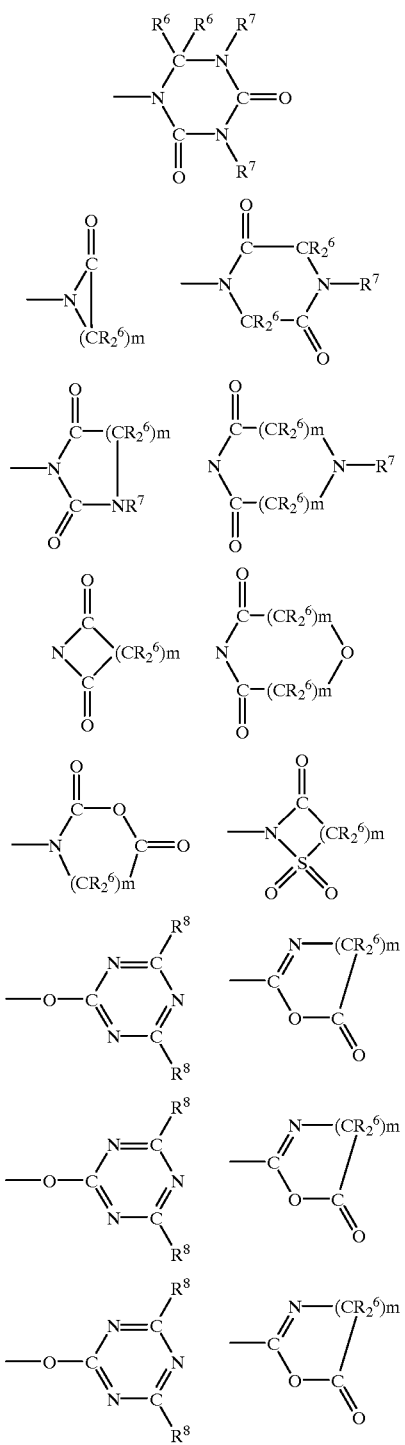

in which each $R^6$ is the same or different and is hydrogen or lower alkyl (optionally substituted), m is an integer of one or more such that the heterocyclic ring has a ring size of up to 10 atoms, preferably 5–8 atoms, the or each $R^7$ is independently selected from hydrogen, optionally substituted lower alkyl, optionally substituted lower acyl, optionally substituted lower alkoxy, optionally substituted lower acyloxy and a group CO—$R^1$—$R^5$ in which $R^1$ and $R^5$ have the same meanings as in formula I, the or each $R^8$ is independently selected from hydrogen, optionally substituted lower alkyl, optionally substituted lower alkoxy and optionally substituted lower acyloxy.

Substituents in any of the above groups may, for instance, increase the solubility, for instance an anionic group, such as a sulphonic acid group, carboxylic acid group, sulphate group, quaternary ammonium group and salts of any of these.

Particularly preferred examples of leaving groups L are lactam groups joined to the rest of the molecule through the nitrogen atom, especially those having a ring size of 5 atoms or more, especially 6–8 atoms. Preferably the alkylene chain joining the carbonyl atom and the nitrogen atom is unsubstituted.

In compounds of the formula I, the group $R^5$ may include a moiety which includes a carbonyl group joined to a leaving group. This may be cleaved in the presence of peroxygen bleaching species to form a further percarboxylic acid moiety. In such compounds the percarboxylic functionality formed in the second reaction may form part of the same molecule as that containing the carbonyl group of the formula I joined to the group L, so that a doubly cleaved molecule is a dipercarboxylic acid. Alternatively the second leaving group may be a component of the acyl group of the percarboxylic acid formed in the first perhydrolytic cleavage, so that two monopercarboxylic acid molecules are formed following the two cleavage reactions. Where the group $R^5$ does include an additional leaving moiety, this may include the said nitrogen-containing heterocycle which is an essential feature of the group $R^5$ in the invention. In such compounds in which $R^5$ can be defined as CO—$L^1$, $L^1$ is preferably selected from the same groups as L. It is preferred for the molecule to be symmetrical, that is $L^1$=L. In some instances it may be desirable for the leaving groups $L^1$ and L to be different, for instance if a different rate of release is desirable.

In the preferred compounds, therefore, where the group $R^5$ includes a group $L^1$ which comprises the nitrogen-containing heterocycle, that heterocyclic group is selected from any of those listed above as suitable examples of the group L in the formula I.

Alternatively the nitrogen containing heterocycle $R^5$ does not form part of a leaving group. In such compounds the group $R^5$ may contain another perhydrolytically cleavable group, but preferably does not, so that the nitrogen containing heterocycle remains as part of the structure of the percarboxylic acid formed when the bond joining the carbonyl carbon atom to the group L of the compound of the formula I is cleaved. In such compounds the nitrogen containing heterocycle of the group $R^5$ may be any of those illustrated above as components of the group L, provided that the linkage to the other atoms of the group $R^5$ or to $R^1{}_1$, as the case may be is not cleavable. This generally requires that where the heterocyclic group is joined to the rest of the molecule by a ring nitrogen atom especially where the ring includes a carbonyl group adjacent to the nitrogen atom, then the heterocycle is joined to a non-carbonyl carbon atom, which is preferably part of an optionally substituted alkylene chain, which may furthermore optionally be interrupted by hetero atoms or arylene groups. For this category of compound, where the heterocycle is joined to a carbonyl carbon atom the nitrogen containing heterocycle should not be one of those types illustrated above as examples of such groups in the group L which is itself cleaved in the perhydrolysis reaction, nor should it be one of the isatoic anhydride-type groups, or one of the 2-substituted oxazine-4-one derivatives.

Preferred examples of the group $R^5$ which contains no further linkage which is perhydrolytically cleavable in the detergent liquor is N-alkyl-lactam, joined to the group $R^1$ through an alkyl chain, N-alkyl imides of dibasic acids, joined through the alkyl group to $R^1$, and piperidine or piperazine attached to $R^1$ through a carbonyl group substituted at the nitrogen atom.

The group $R^5$ having a nitrogen-containing heterocycle which does not form part of a leaving moiety may have, as a substituent in the nitrogen-containing heterocycle a group —$R^9$—CO—$L^3$, in which $L^3$ is a leaving group, the conjugate acid of which has a $pK_a$ in the range 4–13 (preferably 6–11, more preferably 8–11) and which is preferably selected from the groups represented by groups L, and is most preferably identical to the group L, $R^9$ is selected from the same groups represented by $R^1$, and is preferably identical to $R^1$. Such compounds are preferably symmetrical, that is $L^3$=L and $R^9$=$R^1$, and $R^5$ is a symmetrical divalent group.

In this aspect of the invention, it is particularly preferred for $R^1$ to represent an unsubstituted $C_{4-12}$-alkylene group and for $R^5$ to represent CO—$L^1$, in which $L^1$=L. In another embodiment of this aspect $R^5$ is CO—$L^1$ and $R^1$ is an alkylene chain interrupted by at least one anhydride (usually carboxylic anhydride) linkage. The compound is thus a derivative of a polycarboxylic polyanhydride as described in our earlier publication no. WO-A-93/06203.

The compounds of the formula I may be found by acylation of a compound H—L with an appropriate acylating agent, which is, for instance, a derivative of the carboxylic acid $R^5$—$R^1$—COOH or, where $R^5$ is COL, the dibasic carboxylic acid $HOCOR^1COOH$. Such a derivative is usually an acid halide or anhydride.

In a second aspect of the present invention novel monoperacids are provided having the formula II

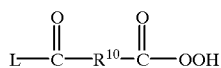

II in which L is as defined above and $R^{10}$ is a $C_{1-50}$ alkylene group, optionally interrupted by one or more ether, ester, anhydride, thioether, 2° or 3° amine, amide or imide linkages or arylene groups, and which may be substituted or unsubstituted.

The compound of the formula II may be synthesised using techniques analogous to those known for producing activators and percarboxylic acids. For instance the corresponding carboxylic acid may be reacted with hydrogen peroxide in the presence of a catalyst, usually an acid catalyst, to form the peroxy acid derivative.

The compound of the formula II may be incorporated into a detergent composition as a bleaching composition. It may be incorporated into such compositions in the form of its salt, for instance stabilised magnesium salts.

More usually the compound of the formula II is formed in situ by the reaction between a peroxygen bleach source and an appropriate activator, that is a compound in which the OOH groups is replaced by a leaving group $L^2$. Appropriate activators may be represented by the formula IV

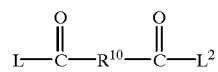

IV in which L and $R^{10}$ are as defined for formula II in which $L^2$ is a leaving group the conjugate acid of which has pKa in the range 4 to 13, preferably 6–11, more preferably 8 to 11. The activator IV may therefore be any N-acyl or O-acyl type compound known to be useful as activators. Examples of suitable leaving groups are selected from those defined in our published specification, no. WO94/18298, the content of which is incorporated herein by reference. Such activators are part of the present invention, as are processes in which they are reacted with a peroxygen bleach source in aqueous solution.

Preferably the activator would comprise a leaving group L as defined above with reference to compound I.

Generally the compound of the formula II, when produced in situ by reaction of an activator with a peroxygen bleach source, is an intermediate and reacts in a second stage in which leaving group L is cleaved in a perhydrolysis reaction to produce a diperoxy dicarboxylic acid.

In a further aspect of the present invention a monopercarboxylic acid of the formula III is provided:

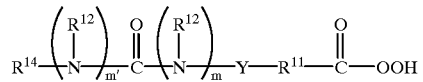

III in which m is 1 and M' is 0 or M' is 1 and m is 0, and $R^{12}$ and $R^{14}$ are each selected from optionally substituted alkylene groups, having 1–4 carbon atoms, and which are joined to one another, optionally through an oxygen atom, carbonyl group, optionally substituted nitrogen atom, lower alkylene group, or any combination of two or more thereof. Preferably each of $R^{14}$ and $R^{12}$ represents an unsubstituted alkylene group and m is 1, so that together an unsubstituted lactam ring is formed with the nitrogen atom and carbonyl carbon atom to which $R^{14}$ and $R^{12}$ are attached.

$R^{11}$ represents a $C_{1-50}$- alkylene group and Y represents a bond or, when m is 1, may represent a carbonyl group. The group $R^{11}$ may optionally be interrupted by one or more arylene group or ether, ester, anhydride, thioether, amide, imide or amine linkages.

In one embodiment of this third aspect of the invention the group

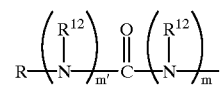

is part of a leaving group. In such compounds, m preferably is 1 and Y represents a carbonyl group.

Just as for compounds of the formula II of the second aspect of this invention, percarboxylic acids of the formula III may either be synthesised using techniques analogous to those used to form peroxycarboxylic acids. The compound may be incorporated as such or in its salt form into detergent compositions.

More usually, the percarboxylic acid of the formula III is produced in situ by reaction of a suitable activator with a peroxygen bleach source. Such activators may be represented by the formula V

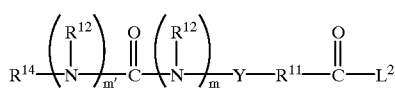

V in which $R^{14}$, $R^{12}$, m, m', Y and $R^{11}$ are as defined for formula III in which $L^2$ is a leaving group the conjugate acid of which has pKa in the range 4 to 13, preferably 6–11, more preferably 8 to 11.

Leaving groups $L^2$ on such activators may thus be any of those described for producing compounds of the formula II. Such activators are included within the scope of the present invention as are processes in which they are reacted with a peroxygen bleach source in aqueous solution.

Where the group

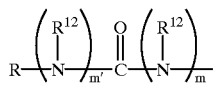

is a leaving group, the compound of the formula III produced in situ is a transient intermediate which is perhydrolysed upon cleavage of the bond joining the carbonyl group Y to the nitrogen atom, to form a dipercarboxylic acid. A detergent liquor formed in such a reaction will include as active oxidising (bleaching) moieties the percarboxylic acid group of the compound of the formula III, as well as both the percarboxylic acid moieties of the product of the second perhydrolysis step of that compound.

The present invention includes within its scope aqueous bleaching liquors comprising a compound of the formula II or III. The invention also comprises compositions containing a compound of the formula I, II or III and a peroxygen bleach source. Furthermore the invention includes within its scope a process in which a compound of the formula II or III in which m is 1 and Y is a carbonyl group, is reacted with a peroxygen bleach source in aqueous solution, so as to cleave the bond between the carbonyl group and $L^1$ or between Y and the nitrogen atom to which it is attached, as the case may be, to form the percarboxylic acid. The present invention comprises also a detergent additive, eg a bleaching composition containing a compound of the formula II or III or an alkali metal, ammonium or alkaline earth metal salts thereof.

In a detergent additive composition according to the invention, the activator of the formula I, IV or V or compound of the formula II or III or salt thereof, is generally formulated such that it is protected from its environment in the composition, in order to render it storage stable. The compound may therefore be formulated by granulating, agglomerating, encapsulating, coating or otherwise protecting it with appropriate detergent components. The compounds may be coformulated with builders, complexing or sequestering agents, especially heavy metal sequesterants such as poly(methylene phosphonic acids), enzymes, surfactants, soaps, soil suspending agents, hydrotopes, mineral oil and foam regulators.

The detergent additive comprising the compound of any of the formulae I–V may be incorporated into any type of bleaching or detergent composition. The composition preferably contains a peroxygen source, although in some instances it may be more convenient to use, as a separate composition, a formulation comprising the peroxygen source the two compositions being added to water to create the wash liquor. Other components of bleaching and detergent compositions include surfactants, usually builders, sequestering agents, foam regulators, enzymes, optical brightening agents, soil suspending agents and anti-redeposition aids, processing aids etc. The compound may be used in conjunction with co-activators, for instance other peroxygen bleach activators such as tetra acetylethylene diamine (TAED), alkanoyloxy benzene sulphonates or tetraaceytyl glycol uril (TAGU) or preformed peracids such as PAP, or with transition metal catalysts or organic catalysts such as enzymes or any other activating moiety.

The present invention is illustrated in the following examples.

General Method of Preparation of Diacyl Lactams

A 1 litre three-necked flask equipped with stirrer, thermometer and reflux condenser was charged with 1 mol of General Method of Preparation of Diacyl Lactams A 1 litre three-necked flask equipped with stirrer, thermometer and reflux condenser was charged with 1 mol of the corresponding lactam, 0.21 mol of the corresponding diacid chloride and 343 g of toluene. The mixture was then heated to reflux and maintained at reflux for a period of 2–5 hours. The mixture was cooled to room temperature and filtered to remove the white solid precipitated. The toluene was removed from the filtrate and 100 cm$^{-3}$ of dichloromethane was added. This organic mixture was washed with water (2×75 cm$^{-3}$), dilute HCl solution (2×75 cm$^{-3}$). Dilute sodium hydrogen carbonate solution (3%) (2×75 cm$^{-3}$) and finally again with water (1×75 cm$^{-3}$). The organic layer was dried over a suitable desiccant and the dichloromethane removed. In some cases, in order to obtain a material or sufficient purity, it was found necessary to re-dissolve the residue in acetone and re-precipitate the product by adding water.

EXAMPLE 1

1.6-dicaprolactam adipate

The title compound is a compound of the formula I in which the group L is N-caprolactam and in which $R^1$ is 1,4-butylene, and $R^5$ is —CO—$L^1$, where L and $L^1$ are N-caprolactam.

It is made from adipoylchloride and caprolactam using the General metho above.

EXAMPLE 2

Di-pyrrolidiononyl adipate

The title compound is a compound of the formula I in which $R^1$ is a 1,4-butylene group, $R^5$ is a group CO—$L^1$ and L and $L^1$ are the same and represent N-pyrrolidone.

The title compound is made by the General method.

EXAMPLE 3

Di-pyrrolidonyl sebacate

The title compound is a compound of the formula I in which the group $R^1$ is a 1,8-octylene group, $R^5$ represents a CO—$L^1$ group in which both the groups L and $L^1$ represent N-pyrrolidone groups.

The title compound is made by the General method to give the product having a melting point of 86.5–88.5° C.

EXAMPLE 4

Dicaprolactam sebacate

The title compound is a compound of the formula I in which the group $R^1$ represents a 1,8-octylene group, $R^5$ represents a CO—$L^1$ group and both groups L and $L^1$ represent N-caprolactam.

The title compound is made by the General method.

EXAMPLE 5

δ-divalerolactam sebacate

The title compound is a compound of the formula I in which the group $R^1$ represents a 1,8-octylene group, $R^5$ represents a CO—$L^1$ group in which both L and $L^1$ are the same and represent N-δ-valerolactam.

The title compound is made by the General method to give the product which has a melting point of 69–70° C.

EXAMPLE 6

N-(N'N'-phthalimidyl-6-aminohexanoyl)-caprolactam

The title compound is a compound of the formula I in which L represents an N-caprolactam group, $R^1$ represents a 1,5-pentylene group and $R^5$ represents an N phthalimide group.

The title compound is made by the following process.

Method of Preparation of Example 6

A solution of the N,N-phthalimidyl-6-aminohexanoyl chloride (0.191 mol) in 54 g of dichloromethane was carefully added to a solution of triethylamine (0.297 mol) (TEA) and caprolactam (0.194 Mol) in 200 cm$^{-3}$ of toluene. Once the addition was completed, the dichloromethane and excess TEA was removed from the mixture and the residue heated to reflux and maintained at reflux for a period of 3 hours. The mixture was cooled to room temperature and washed with water (2×150 cm$^{-3}$). The aqueous phases were combined and extracted with (1×50 cm$^{-3}$) of toluene. The toluene phases were bulked and the toluene removed to give an orange oil. This crude product was distilled, collecting the fraction distilling at 246° C.–250° C. at a 10 mm Hg (1.3 kPa) vacuum. This was in the form of a gel.

EXAMPLE 7

Performance Tests

Products of examples 1–3 and 6 are subjected to performance tests to determine their ability to bleach stained swatches. The tests were carried out as follows.

The wash tests were undertaken at 40 and 60° C. using cold fill Wascator FOM 71 MP machines, programmed to BS 4923 (HLCC) wash programmes. Formulations contained 22.5 g sodium perborate tetrahydrate, 124.5 g of IEC standard base detergent and a fixed amount of activator such that the same equivalents as TAED (about 5% by weight) would be available. Formulations were closed at 7.5 g/l via the dispensing drawer of the machines.

All washes contained 2.5 kg of polyester backing cloth to which the swatches were tagged, using plastic tags. Swatches were made from cotton fabric. Swatches measured 12 cm×12 cm. After washing the swatches were removed and ironed dry prior to reading the reflectance.

Due to variations n swatch make up all evaluations were run compared to a TAED standard using swatches from the same batch. The stain removal was assessed visually in these tests.

The results indicated that example 3 gave excellent results (as did the comparison compound TAED) and examples 1, 2 and 6 gave good results.

We claim:
1. A composition containing
(i) a compound having the formula I

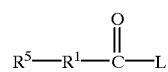

I in which L is a leaving group the conjugate acid of which has $PK_a$ in the range of from 4–13 and which is a nitrogen containing heterocycle where the heterocyclic ring includes one or two carbonyl groups joined to the said nitrogen atom and in which the group L is joined to the carbonyl carbon atom in the formula via the ring nitrogen atom;

$R^1$ is an alkylene group having 1–50 carbon atoms, optionally interrupted by one or more linkages selected from the group consisting of ether, ester, anhydride, thioether, 2° and 3° amine, amide and imide linkages; and $R^5$ comprises a nitrogen-containing heterocycle where the heterocyclic ring includes one or two carbonyl groups joined to the said nitrogen atom;

(ii) a peroxygen bleach source;
(iii) surfactant;
(iv) builder; and
(v) sequestrant.

2. A composition according to claim 1 in which in the compound I, $R^5$ is an N-alkyl heterocycle selected from the group consisting of N-alkyl lactams and N-alkyl imides whereby the group $R^5$ is joined through the said alkyl group to $R^1$.

3. A composition according to claim 1 in which in the compound I, $R^5$ is —CO—$L^1$ in which $L^1$ is independently selected from the same groups as L.

4. A composition according to claim 3 in which in the compound I, $L^1$ is the same as the group L.

5. A process in which a compound having the formula I

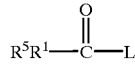

I in which L is a leaving group the conjugate acid of which has $PK_a$ in the range of from 4–13 and which is a nitrogen containing heterocycle where the heterocyclic ring includes one or two carbonyl groups joined to the said nitrogen atom and in which the group L is joined to the carbonyl carbon atom in the formula via the ring nitrogen atom;

$R^1$ is an alkylene group having 1–50 carbon atoms, optionally interrupted by one or more linkages selected from the group consisting of ether, ester, anhydride, thioether, 2° and 3° amine, amide and imide linkages; and $R^5$ comprises a nitrogen-containing heterocycle where the heterocyclic ring includes one or two carbonyl groups joined to the said nitrogen atom, is contacted in aqueous solution with a peroxygen bleach source to form a solution containing an oxidising species which is a stronger oxidising species than the peroxygen source.

6. A process according to claim 5 in which $R^5$ is an N-alkyl heterocycle selected from the group consisting of N-alkyl lactams and N-alkyl imides, whereby the group $R^5$ is joined through the said alkyl group to $R^1$.

7. A process according to claim 5 in which $R^5$ is —CO—$L^1$ in which $L^1$ is independently selected from the same groups as L.

8. A process according to claim 7 in which $L^1$ is the same as the group L.

9. A compound having the formula I

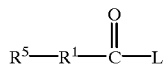   I in which L is a leaving group the conjugate acid of which has $pK_a$ in the range of from 4–13 and which is a nitrogen containing heterocycle where the heterocyclic ring includes one or two carbonyl groups joined to the said nitrogen atom and in which the group L is joined to the carbonyl carbon atom in the formula via the ring nitrogen atom;

$R^1$ is an alkylene group having 1–50 carbon atoms, optionally interrupted by one or more linkages selected from the group consisting of ether, ester, anhydride, thioether, 2° and 3° amine, amide and imide linkages; and $R^5$ comprises a nitrogen-containing heterocycle where the heterocyclic ring includes one or two carbonyl groups joined to the said nitrogen atom.

10. A compound according to claim 9 wherein the said nitrogen containing heterocycle is selected from the group comprising uracils, hydantoins, glycol urils, 2,5- diketopiperazine and N-lactam groups.

11. A compound according to claim 9 in which $R^5$ is an N-alkyl heterocycle selected from the group consisting of N-alkyl lactams and N-alkyl imides, whereby the group $R^5$ is joined through the said alkyl group to $R^1$.

12. A compound according to claim 9 in which $R^5$ is —CO—$L^1$ in which $L^1$ is independently selected from the same groups as L.

13. A compound according to claim 12 in which $L^1$ is the same as the group L.

14. A compound according to claim 9 in which L is

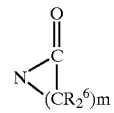

in which $R^6$ is hydrogen, optionally substituted lower alkyl; and m is an integer of two or more such that the heterocyclic ring has a ring size of 4–10 atoms.

15. A compound according to claim 14 in which m is an integer in the range 3 to 6.

* * * * *